(12) United States Patent
Björling

(10) Patent No.: US 8,761,882 B2
(45) Date of Patent: Jun. 24, 2014

(54) IMPLANTABLE HEART STIMULATING DEVICE AND METHOD

(75) Inventor: Anders Björling, Solna (SE)

(73) Assignee: St. Jude Medical AB, Jarfalla (SE)

( * ) Notice: Subject to any disclaimer, the term of this patent is extended or adjusted under 35 U.S.C. 154(b) by 701 days.

(21) Appl. No.: 12/299,821

(22) PCT Filed: May 16, 2006

(86) PCT No.: PCT/SE2006/000568
§ 371 (c)(1),
(2), (4) Date: Nov. 6, 2008

(87) PCT Pub. No.: WO2007/133130
PCT Pub. Date: Nov. 22, 2007

(65) Prior Publication Data
US 2009/0204169 A1    Aug. 13, 2009

(51) Int. Cl.
*A61N 1/362* (2006.01)
(52) U.S. Cl.
USPC .................................... 607/28; 607/9
(58) Field of Classification Search
USPC ................. 607/27, 28, 29–32, 13, 9; 600/509
See application file for complete search history.

(56) References Cited

U.S. PATENT DOCUMENTS

| | | | |
|---|---|---|---|
| 3,920,024 A * | 11/1975 | Bowers | 607/28 |
| 4,969,460 A | 11/1990 | Callaghan et al. | |
| 5,476,487 A * | 12/1995 | Sholder | 607/28 |
| 5,720,768 A | 2/1998 | Verboven-Nelissen | |
| 6,070,100 A | 5/2000 | Bakels et al. | |
| 6,473,649 B1 * | 10/2002 | Gryzwa et al. | 607/28 |
| 6,782,291 B1 | 8/2004 | Bornzin et al. | |
| 6,947,794 B1 | 9/2005 | Levine | |
| 6,975,904 B1 | 12/2005 | Sloman | |
| 2004/0088018 A1 | 5/2004 | Sawchuk | |
| 2004/0116971 A1 * | 6/2004 | Bjorling et al. | 607/9 |
| 2005/0137640 A1 | 6/2005 | Freeberg et al. | |
| 2006/0241710 A1 | 10/2006 | Rueter | |

FOREIGN PATENT DOCUMENTS

EP    1 430 928    6/2004

OTHER PUBLICATIONS

Supplementary EP Search Report, dated Nov. 12, 2012—EP Application No. 06747785.1.

* cited by examiner

*Primary Examiner* — Joseph Stoklosa

(57) ABSTRACT

In an implantable heart stimulating device and a method of the operation thereof, device has a control circuit that detects an evoked responses to delivered pacing pulses and to carry out an automatic capture routine. The control circuit is arranged to automatically temporarily disable the automatic capture routine on the basis of at least one of the following criteria:
- a1) if more than a predetermined number of threshold searches have been performed during a certain time, and
- b1) if a variable time delay with which the device operates is changed such that a pacing pulse may be delivered by the device during the evoked response time window.

22 Claims, 2 Drawing Sheets

IMPLANTABLE HEART STIMULATING DEVICE AND METHOD

BACKGROUND OF THE INVENTION

1. Field of the Invention

The present invention relates to an implantable heart stimulating device with means for detecting an evoked response to delivered pacing pulses.

The invention also relates to a method of operating an implantable heart stimulating device.

2. Description of the Prior Art

Several different implantable devices for stimulating a heart are known. The devices are normally able to sense the electrical activity of the heart. Some implantable devices are able to deliver stimulation pulses to and/or sense the right atrium (in some cases even the left atrium) and also to deliver stimulation pulses to and sense one or both of the left and right ventricles. Devices that are able to deliver stimulation pulses to both the left and right ventricles can be called bi-ventricular pacers. Such devices can be used to treat patients who suffer from different severe cardiac problems, e.g. patients suffering from congestive heart failure (CHF). CHF is defined generally as the inability of the heart to deliver a sufficient amount of blood to the body. CHF can have different causes. It can for example be caused by a left bundle branch block (LBBB) or a right bundle branch block (RBBB). By using bi-ventricular pacing, the contraction of the ventricles can be controlled in order to improve the ability of the heart to pump blood. The stimulation pulses to the two ventricles can be delivered simultaneously, but it is also known that the stimulation pulses to the two ventricles are delivered with a short time delay (VV) between them in order to optimize the pumping performance of the heart.

U.S. Pat. No. 5,720,768 describes different possible electrode positions in order to stimulate or sense the different chambers of the heart.

U.S. Pat. No. 6,070,100 describes that electrodes may be positioned in both the left and the right atrium as well as in the left and the right ventricle.

In connection with implantable pacers, it is known to detect the capture of the heart, i.e. to detect whether the heart actually reacts on a delivered stimulation pulse. This detection is also called evoked response (ER) detection. If the heart is not captured, it is possible to arrange the pacer to deliver a back-up pulse with a higher pulse energy than the first pulse. It is also possible to increase the pulse energy in future stimulation pulses if capture is not detected. In order to save battery it is important that the stimulation pulses are not delivered with an unnecessarily high energy. In order to determine a suitable pulse energy, it is known to perform an automatic threshold/capture search. By varying the energy of the stimulation pulses, and by detecting whether capture occurs, it is thus possible to find a threshold value for the stimulation pulse energy. Based on the threshold value, a suitable stimulation pulse energy can be determined.

U.S. Pat. No. 6,782,291 describes an implantable cardiac stimulation device that senses evoked responses to applied pacing stimulation pulses. A pulse generator applies the stimulation pacing pulses to the heart in accordance with a pacing configuration. A sensor control selects an evoked response sensing electrode configuration from among a plurality of evoked response sensing electrode configurations in response to the pacing configuration. Signal-to-noise ratios obtained with the various electrode configurations are used to select a best electrode configuration for sensing evoked responses. If no electrode configuration yields an acceptable signal-to-noise ratio, it is recommended that the evoked response sensing be programmed off.

U.S. Pat. No. 6,473,649 describes an implantable cardiac rhythm management device capable of automatically detecting intrinsic and evoked response of a patient's heart and suitable for use during capture verification. The device may operate in an automatic capture verification mode, wherein an electrocardiogram signal of a patient's heart is received and used by the device to determine whether a stimulation pulse evokes a response by the patient's heart. The device suspends the automatic capture verification mode and/or adjusts the detection threshold dependent upon detected and/or measured noise, a determined amplitude of evoked response, a determined modulation in the evoked response, or detected and/or measured artifact.

U.S. Pat. No. 6,975,904 describes the optimization of evoked response detection in an automatic capture detection system employed by an implantable cardiac stimulation device. In one aspect, an automatic capture detection function may be temporarily disabled in order to prevent an inaccurate loss of capture detection while a patient is in the process of changing position, or when the sensed activity level exceeds some threshold value. For example, the ER signal morphology may be undetectable during a shift in position by a patient or when the patient is too active, i.e., where the ER is changing a significant amount. The automatic capture detection function may be temporarily disabled to account for an undetectable ER signal, thus preventing an erroneous loss of capture detection by the automatic capture detection system.

A heart stimulation device sold under the name "Regency" by St Jude Medical (formerly by Pacesetter AB) has a so-called autocapture function that includes automatic verification of capture and adaptation to changing detection thresholds. In this device the autocapture algorithm is temporarily disabled when the simulation threshold is above a certain level (e.g. above 3.9 V). Stimulation is then set to a high output (e.g. 4.5 V). Furthermore, in this device the autocapture algorithm is temporarily disabled when noise is detected and for as long as the noise is sensed.

SUMMARY OF THE INVENTION

The present invention represents an improvement over an implantable heart stimulating device of the type having a control circuit that includes a first pacing circuit that communicates with a first pacing electrode positioned in or at a first heart chamber, with the first pacing circuit pacing the first heart chamber via the first pacing electrode, and having a first sensing circuit that communicates with one or more sensing electrodes or sensors positioned with respect to the first heart chamber, the control circuit detecting an evoked response to a pacing pulse delivered by the first pacing circuit by sensing, with the first sensing circuit, within a first time window that follows after a pacing pulse delivered by the first pacing circuit. The control circuit operates with time cycles corresponding to cardiac cycles, and the control circuit executes an automatic capture routine that includes an adaptation of a pacing regime, which involves the first pacing circuit, dependent on the sensing with the first sensing circuit during the first time window.

The present invention is based on the insight that such a device there is room for further improvement concerning the use of such an automatic capture routine. The inventor has thus found that during certain circumstances it may be beneficial not to use the automatic capture routine. An object of the invention is therefore to use an automatic capture routine in an optimal manner and to disable (switch off) the automatic capture routine under certain circumstances. A further object is to provide such a device that uses the automatic capture routine only when it is likely to be beneficial. Another object is to provide such a device that in a relatively simple manner can switch on or off such an automatic capture routine.

The above objects are achieved by an implantable heart stimulating device of the mentioned type, wherein the control circuit is arranged to automatically temporarily disable the automatic capture routine of said first pacing circuit and said first sensing circuit on the basis of at least one of the following criteria:

a1) if the control circuit automatically performs more than a predetermined number of threshold searches with said first pacing circuit and said first sensing circuit during a certain time, b1) if the evoked response signals sensed by said first sensing circuit vary more than a predetermined amount over a certain number of time cycles, c1) if a certain variable time delay with which the device operates is changed such that a pacing pulse may be delivered by the device during said first time window in such a manner that the detection of the evoked response with said first sensing circuit during said first time window is likely to be unreliable.

The invention is based on the insight that if too many threshold searches are automatically performed by the device during a certain time, this may be an indication of the fact that it is advantageous to switch off the automatic capture routine and to operate the device without such a routine. Similarly, if the evoked response signals vary to a large extent, even if capture is indicated, then it may be advantageous to switch off the automatic capture routine. Furthermore, if the device operates with a variable time delay that is changed such that pacing pulses are delivered to other parts of the heart during the time window when sensing is performed concerning the first heart chamber, then the automatic capture routine may not work very well and it may therefore be advantageous to switch off this routine.

The device according to the invention may thus be arranged to include one or more of the criteria a1), b1) and c1). According to an embodiment, the device includes all these three criteria (the device can of course also include further criteria) and the automatic capture routine is switched off as soon as at least one of these criteria is fulfilled.

According to an embodiment of the implantable heart stimulating device according to the invention, the control circuit has a second pacing circuit, adapted to communicate with a second pacing electrode suited to be positioned in or at a second heart chamber, wherein the second pacing circuit is adapted to enable pacing of such a second heart chamber. It is of course advantageous if the device is able to pace more than one heart chamber.

According to a further embodiment of the implantable heart stimulating device according to the invention, the control circuit has a second sensing circuit, adapted to communicate with one or more sensing electrodes or sensors suited to be positioned in or in relation to said second heart chamber, the control circuit being arranged to be able to detect an evoked response to a pacing pulse delivered by said second pacing circuit by sensing, with said second sensing circuit, within a second time window that follows after a pacing pulse delivered by said second pacing circuit. The control circuit is adapted to carry out an automatic capture routine which includes an adaptation of a pacing regime, which involves the second pacing circuit, in dependence on the sensing with the second sensing circuit during the second time window. Evidently, it is advantageous if the device is arranged to be able to pace and sense more than one heart chamber. The device can be provided with means for pacing and sensing two, three or all four chambers of the heart. It is thereby advantageous if the device is arranged to be able to carry out an automatic capture routine for each such chamber.

It can be noted that the automatic capture routine (for each heart chamber) can involve different features, for example the delivery of a back-up pacing pulse with the pacing circuit in question if no evoked response is sensed within the relevant time window. The automatic capture routine can also include threshold searches. It can for example involve a pacing regime that means that if no evoked response is detected during the evoked response time window, then the pulse energy of the pacing pulse is increased in the next time cycle. The pulse energy can for example be increased more and more for each time cycle until capture is detected. A threshold search can also be performed by starting with a high pulse energy, and then step down in energy in order to find a threshold value for achieving capture. The device is normally arranged to automatically carry out some kind of threshold search when, for example, no evoked response has been detected during a certain number of time cycles. The automatic capture routine thus has different optional features. However, it is always the case that the automatic capture routine involves the adaptation of some pacing regime in dependence on the sensing with the sensing circuit in question during the relevant evoked response time window.

According to a further embodiment of the implantable heart stimulating device according to the invention, the control circuit is arranged to automatically temporarily disable the automatic capture routine of the second pacing circuit and the second sensing circuit on the basis of at least one of the following criteria:

a2) if the control circuit automatically performs more than a predetermined number of threshold searches with the second pacing circuit and the second sensing circuit during a certain time, b2) if the evoked response signals sensed by the second sensing circuit vary more than a predetermined amount over a certain number of time cycles, c2) if a certain variable time delay with which the device operates is changed such that a pacing pulse may be delivered by the device during said second time window in such a manner that the detection of the evoked response with said second sensing circuit during the second time window is likely to be unreliable.

According to this embodiment, the device is thus arranged to be able to disable the automatic capture routine also concerning a second heart chamber. The device can of course be arranged with such routines for each heart chamber to which the device delivers pacing pulses.

It should be noted that the first and second pacing circuits and the first and second sensing circuits may partly include the same components. For example, the same sense amplifier can be used both for the first and second sensing circuits. Alternatively, separate sense amplifiers can be used for the first and second sensing circuits. The concepts "first" and "second" are thus used in order to at least functionally distinguish between the different "circuits".

When the automatic capture routine is disabled, the pacing pulses can, for example, be delivered with a relatively high energy, such that the heart chamber in question is likely to capture.

According to a further embodiment of the implantable heart stimulating device according to the invention, the control circuit is arranged such that said automatic capture routines related to the first pacing and sensing circuits and to the second pacing and sensing circuits operate independently of each other such that the automatic capture routine is automatically temporarily disabled only in that pacing/sensing channel where the criterion or criteria indicate that the automatic capture routine should be temporarily disabled. It is a particular advantage of the present invention that the automatic capture routine is only disabled in that particular channel where it is necessary. The automatic capture routine can thus continue for the other heart chambers.

According to a further embodiment of the implantable heart stimulating device according to the invention, the control circuit is arranged to temporarily disable the automatic capture routine on the basis of at least the criteria c1), wherein the variable time delay is an AV delay, which is the delay between an atrial event and the delivery of a ventricular pacing pulse, wherein the first heart chamber is an atrium, such that said first pacing circuit and the first sensing circuit relate to an atrial channel of the device and said second heart chamber is a ventricle, such that the second pacing circuit and the second sensing circuit relate to a ventricular channel of the device. If the AV delay is changed such that a possible pacing pulse delivered with said second pacing circuit will be delivered during the first time window in such a manner that the detection of the evoked response with the first sensing circuit during the first time window is likely to be unreliable, then the automatic capture routine which is related to said first pacing and sensing circuits will be temporarily disabled. This embodiment of the invention is thus particularly useful for a device that delivers pacing pulses to an atrium and that operates with a variable AV delay.

According to a further embodiment of the implantable heart stimulating device according to the invention, the control circuit is arranged to temporarily disable the automatic capture routine on the basis of at least the criteria c1), wherein the variable time delay is a VV delay, which is the delay between a ventricular event related to one ventricular channel of the device and the delivery of a ventricular pacing pulse by another ventricular channel of the device. The first heart chamber is one ventricle, such that the first pacing circuit and the first sensing circuit relate to one ventricular channel of the device and the second heart chamber is another ventricle, such that the second pacing circuit and the second sensing circuit relate to another ventricular channel of the device. If the VV delay is changed such that a possible pacing pulse delivered with the second pacing circuit will be delivered during the first time window in such a manner that the detection of the evoked response with the first sensing circuit during the first time window is likely to be unreliable, then said automatic capture routine which is related to said first pacing and sensing circuits will be temporarily disabled. This embodiment of the invention is thus particularly useful for a device that delivers pacing pulses to both ventricles of the heart and that operates with a variable VV delay.

When it is stated herein that the AV or VV delay ends with the delivery of a pacing pulse, this definition of course includes the possibility that the "delivered" pacing pulse may be inhibited, if an intrinsic event is sensed.

The device may of course work both with a variable AV delay and a variable VV delay. In this case it is possible to combine the above described embodiments such that the automatic capture routine is disabled in one or both of an atrial channel and a ventricular channel depending on the AV and VV delays, respectively.

According to a further embodiment of the implantable heart stimulating device according to the invention, the control circuit is arranged to temporarily disable the automatic capture routine on the basis of at least the criteria a1) and/or a2) and wherein the control circuit is arranged to automatically end the temporary disablement of the respective automatic capture routine on the basis of at least one of the following criteria: if a certain predetermined time has passed, if the evoked response signals sensed by said first or second sensing circuit, respectively, vary less than a predetermined amount over a certain number of time cycles.

If a certain time has past, it may be beneficial to switch on the automatic capture routine again in order to see if the operational situation of the device has become more stable. Similarly, if evoked response signals have been sensed when the automatic capture routine was switched off, then, if the sensed signals appear to be stable, it can be beneficial to switch on the automatic capture routine again.

According to a further embodiment of the implantable heart stimulating device according to the invention, the control circuit is arranged to temporarily disable the automatic capture routine on the basis of at least the criteria b1) and/or b2) and wherein the control circuit is arranged to automatically end the temporary disablement of the respective automatic capture routine on the basis of at least one of the following criteria: if a certain predetermined time has passed. If the evoked response signals sensed by said first or second sensing circuit, respectively, vary less than a predetermined amount over a certain number of time cycles. Similarly to the previous embodiment, it can be advantageous to switch on the automatic capture routine if a certain time has passed or if the situation appears to have become more stable.

According to a further embodiment of the implantable heart stimulating device according to the invention, the control circuit is arranged to temporarily disable the automatic capture routine on the basis of at least the criteria c1) and/or c2) and wherein the control circuit is arranged to automatically end the temporary disablement of the respective automatic capture routine when said time delay has changed such that it is no longer the case that a pacing pulse may be delivered by the device during the first or second time window, respectively, in such a manner that the detection of the evoked response with said first or second sensing circuit, respectively, during the first or second time window, respectively, is likely to be unreliable. According to this embodiment, it is appropriate to switch on the automatic capture routine again when the AV or VV delay has changed such that it is no longer the case that pacing pulses may be delivered during the evoked response time window in question.

Concepts like atrial, atrial event, ventricular, pacing pulses, related to a first heart chamber etc. are used herein to functionally describe the operation of the device. This does not mean that the device is necessarily connected to a heart. The functional concepts are thus used in order to illustrate how the device would function if actually used for stimulating (and sensing) a heart.

A second aspect of the present invention relates to a method of operating an implantable heart stimulating device including the following steps: operate the device with time cycles corresponding to heart cycles, deliver pacing pulses to a first heart chamber, sense evoked responses from the first heart chamber to the delivered pacing pulses by sensing during a first time window that follows after a delivered pacing pulse to the first heart chamber, carry out an automatic capture routine which includes an adaptation of a pacing regime regarding the first heart chamber in dependence on the sensing for evoked responses from said first heart chamber during the first time window.

An object of the second aspect of the present invention is to improve a method of operating an implantable heart stimulating device and to thereby use an automatic capture routine in an optimal manner and to disable (switch off) the automatic capture routine under certain circumstances. A further object is to provide such a method that uses the automatic capture routine only when it is likely to be beneficial. Another object of the method is to provide such a method that in a relatively simple manner can change to and from the use of such an automatic capture routine.

The mentioned objects according to the second aspect of the invention is achieved by temporarily disabling the automatic capture routine for said first heart chamber on the basis of at least one of the following criteria: a1) if more than a predetermined number of threshold searches are automatically performed for said first heart chamber during a certain time, b1) if the sensed evoked response signals from said first heart chamber vary more than a predetermined amount over a certain number of time cycles, c1) if a certain variable time delay with which the device operates is changed such that a pacing pulse may be delivered by the device during said first time window in such a manner that the detection of the evoked response from said first heart chamber during said first time window is likely to be unreliable.

Different manners of carrying out the method according to the invention are clear from the description below and from the dependent method claims.

The method according to the invention has similar advantages to those described above in connection with the device according to the invention.

DESCRIPTION OF THE PREFERRED EMBODIMENTS

Figure 1:
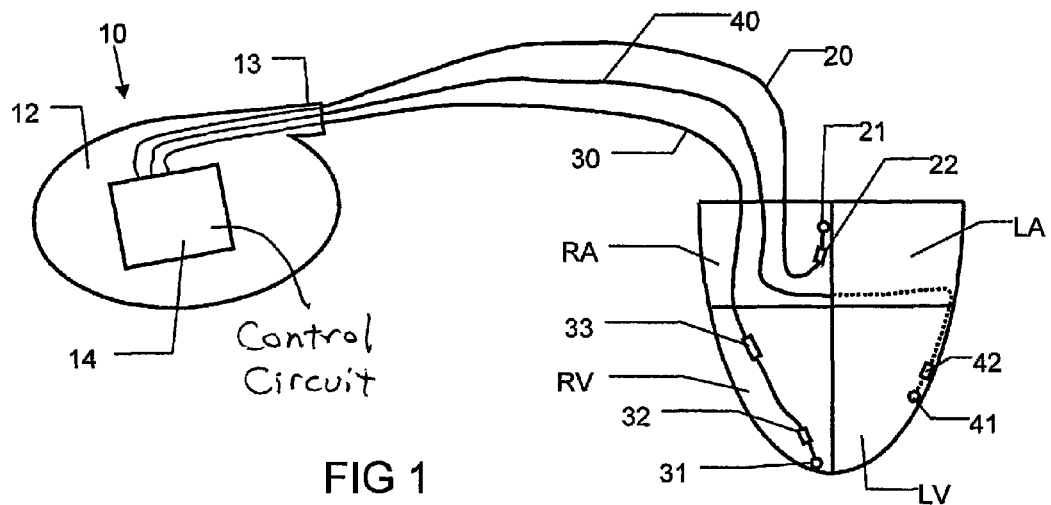
FIG. 1 shows schematically an implantable heart stimulating device connected to leads with sensors and sensing and pacing electrodes positioned in a heart.

FIG. 1 shows schematically an implantable heart stimulating device 10 according to the invention. The device 10 has a housing 12. The device 10 comprises a connector portion 13. Via the connector portion 13, the device 10 can be connected to different leads. In FIG. 1 the device 10 is connected to three leads: 20, 30 and 40.

The lead 20 includes a pacing and sensing electrode 21, 22.

Similarly to the lead 20, the lead 30 includes a pacing and sensing electrode 31, 32. According to this example, the lead 30 also includes a sensor 33, which can be a pressure sensor for sensing the blood pressure.

The lead 40 includes a pacing and sensing electrode 41, 42.

In the shown example, the electrodes 21, 22, 31, 32, 41, 42 are bipolar electrodes with a tip portion 21, 31, 41 and a ring portion 22, 32, 42. However, it is within of the scope of the invention that instead unipolar electrodes can be used. This is known to a person skilled in the art.

The device 10 comprises a control circuit 14, which will be described further below.

The device 10 can also include, or be connected to, more or less sensors than the sensor 33 shown in the figure.

The device 10 together with the leads 20, 30, 40 and the electrodes/sensor 21, 22, 31, 32, 33, 41, 42 constitute a heart stimulating system that can be implanted in a patient.

FIG. 1 also schematically illustrates a heart with a right atrium RA, a left atrium LA, a right ventricle RV and a left ventricle LV.

In the shown example, the electrode 21, 22 constitutes a right atrial sensing and/or pacing electrode 21, 22, which is positioned in the right atrium RA.

The electrode 31, 32 constitutes a right ventricular sensing and pacing electrode 31, 32, which is positioned in the right ventricle RV.

The electrode 41, 42 constitutes a left ventricular sensing and pacing electrode 41, 42, which is positioned the left ventricle LV. The left ventricular sensing and pacing electrode 41, 42 is adapted to enable sensing and pacing of the left ventricle LV. The lead 40 may for example be introduced via the right atrium RA and the coronary sinus such that the electrode 41, 42 is positioned in for example the middle or great cardiac vein of the heart. How to introduce the lead 40 in this manner is known to a person skilled in the art.

It is also possible that the device 10 is connected to further leads and/or further electrodes or sensors, for example electrodes positioned in order to sense and/or pace the left atrium LA and electrodes designed to enable defibrillation.

Figure 2:
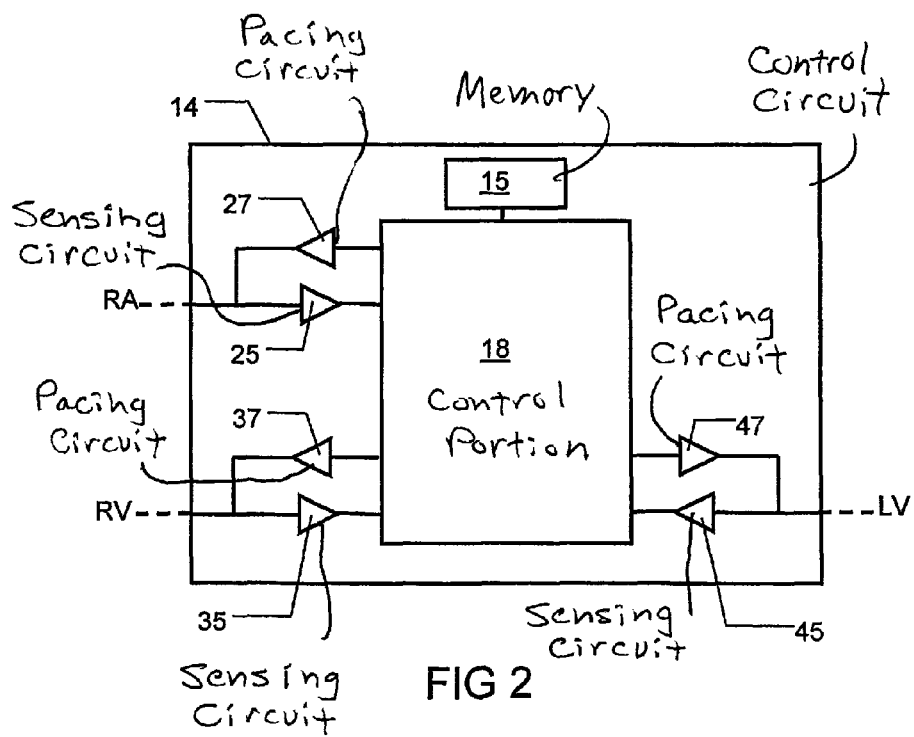
FIG. 2 shows schematically a control circuit which may form part of the device.

FIG. 2 shows schematically the control circuit 14 in some more detail. The control circuit 14 includes a memory 15 connected to a control portion 18.

The control circuit 14 includes a right atrial sensing circuit 25 and a right atrial pacing circuit 27. The right atrial sensing and pacing circuits 25, 27 communicate with the right atrial sensing and pacing electrode 21, 22 via the lead 20. The right atrial sensing and pacing circuits 25, 27 are thus adapted to sense and pace an atrium, in this case the right atrium RA.

The control circuit 14 also includes a right ventricular sensing circuit 35 and a right ventricular pacing circuit 37. These circuits 35, 37 communicate with the right ventricular sensing and pacing electrode 31, 32 via the lead 30. The circuits 35, 37 are thus adapted to sense and pace a ventricle, in this case the right ventricle RV.

The control circuit 14 also includes a left ventricular sensing circuit 45 and a left ventricular pacing circuit 47. These circuits 45, 47 communicate with the left ventricular sensing and pacing electrode 41, 42 via the lead 40. These circuits 45, 47 are adapted to sense and pace a ventricle, in this case the left ventricle LV.

The control circuit 14 is arranged, or programmed, to include several operational features. The control circuit 14 is thus arranged to be able to detect an evoked response to a pacing pulse delivered by a pacing circuit 27, 37, 47 by sensing within a time window ER that follows after a pacing pulse delivered by the pacing circuit in question 27, 37, 47.

How to design a pacer to sense evoked responses is known to a person skilled in the art. The time window ER may for example be set to begin 5 ms to 30 ms, for example 15 ms, after the delivery of a pacing pulse. The length of the time window ER may for example be 30 ms to 70 ms, for example 50 ms.

It should be noted that the time windows ER related to the different heart chambers RA, RV, LV do not necessarily have to have the same length and they do not necessarily have to start or end the same time period after the respective delivered pacing pulse.

The sensing of the evoked response can be done with the help of the respective sensing circuit 25, 35, 45. With the help of the respective sensing circuit 25, 35, 45 and the control portion 18 it is thus possible to sense an evoked response by detecting an electrical signal emitted by the cardiac tissue.

In this context it can be noted that the control circuit 14 can also be arranged to sense the intrinsic P-waves or R-waves (i.e. a depolarisation of the heart that is not caused by a pacing pulse delivered with the help of the device 10). As is known to a person skilled in the art, the control logic can be different for sensing an evoked response and for sensing an intrinsic P-wave or R-wave (QRS complex). The control portion 18 can thus include different such detection logics. Ventricular and/or atrial pacing pulses may be inhibited if intrinsic events are sensed.

An evoked response can also be detected by other means than by detecting electrical signals emitted from the cardiac tissue. Any means of detecting evoked response can be used in connection with the present invention. It is thus for example possible to detect an evoked response with the help of a blood pressure sensor, like the sensor 33. Since the blood pressure in a heart chamber increases when the heart chamber contracts, the blood pressure can be used to detect an evoked response.

Another possibility is to detect an evoked response by sensing the impedance between different points of the body of the patient. For example concerning the shown right ventricle RV, the impedance can for example be sensed between the electrode surfaces 31 and 32, or between one of these electrode surfaces 31, 32 and a further electrode surface (for example located at the position shown for the sensor 33). The impedance measured is related to for example the amount of blood in a heart chamber, and since the amount of blood depends on whether the heart chamber in question has contracted or not, this impedance measurement can be used to detect an evoked response. How an impedance measurements can be carried out is known from the prior art.

It can be noted that the beginning and the end of the evoked response detection window may differ depending on which detection method is used.

Moreover, it can be noted that the signal with which the evoked response is detected can be generated in different manners. For example, if the evoked response detection is based on sensing an electrical signal emitted by the cardiac tissue (i.e. the evoked response detection signal is an IEGM, i.e. an intracardiac electrogram), then the control circuit can for example be arranged to detect evoked response by using of one or more of the following detection calculations/measurements:

how steep the evoked response detection signal is (this can be done by detecting a derivative in the signal), an area defined by the evoked response detection signal (this can be based on an integral and is sometimes called the PDI method), the morphology of the evoked response detection signal, the number of zero crossings in the evoked response detection signal, the time to one or more zero crossings and/or the time between zero crossings in the evoked response detection signal, the maximum or minimum of a peak of the evoked response detection signal, the time to the maximum or minimum of a peak of the evoked response detection signal.

The control circuit 14 is arranged to be able to operate with time cycles corresponding to normal heart cycles. Such an operation is normal for an implantable heart stimulating device. The time cycles are determined by preset timer intervals which also may depend on detected signals The control circuit 14 is also arranged to be able to operate with a normal AV delay (the delay between an atrial paced or sensed event and the delivery of a ventricular pacing pulse). It is also common that the delivery of pacing pulses can be inhibited if intrinsic events are sensed.

The control circuit 14 can also be arranged to, within a time cycle, be able to deliver pacing pules to both the right RV and left LV ventricles, i.e. with the help of the pacing circuits 37 and 47, with a time gap VV between a sensed or paced event of one of sensing/pacing channels 35,37 or 45,47 and the delivery of a pacing pulse (which may also be inhibited) with the other one of said sensing/pacing channels. A typical value of VV can be between 0 ms and 80 ms.

Moreover, the control circuit 14 may be arranged such that the AV and/or VV delay is automatically changed depending on certain inputs. For example, the AV delay made be shortened if the pacing rate increases. The VV delay may for example be changed for making the contractions of the two ventricles occur simultaneously.

Although not described in any detail herein, the control circuit 14 can be arranged to include several other operational features that are known in connection with heart stimulation devices. Such features include, for example, blanking and refractory periods, the ability to sense how physically active the patient in question is, the ability to carry out defibrillation, the ability to communicate with the help of so-called telemetry, etc.

The control circuit 14 is also arranged to carry out an automatic capture routine. This automatic capture routine can for example include the following:

the delivery of a back-up pacing pulse with the pacing circuit in question 27, 37, 47 if no evoked response is sensed within the relevant time window;

if no evoked response is detected during the evoked response time window, then the pulse energy of the pacing pulses is increased in the next time cycle; the pulse energy can for example, be increased more and more for each time cycle until capture is detected in the heart chamber in question;

to perform a threshold search in order to find a value for the pacing pulses, delivered with the pacing circuit in question 27, 37, 47, which value is necessary in order to obtain capture of the heart chamber RA, RV, LV in question; such a threshold search can be performed from time to time even if capture is detected, in order to find out whether it is sufficient to pace the heart chamber with a lower pulse energy.

The automatic capture routine can thus include different features. However, it is always the case that the automatic capture routine involves the adaptation of some pacing regime in dependence on the sensing with the sensing circuit in question during the relevant evoked response time window.

Preferably, the control circuit 14 is arranged to be able to carry out an automatic capture routine concerning each channel of the device 10, i.e. in the shown example, the channels related to the right atrium RA, the right ventricle RV and the left ventricle LV.

According to the invention, the control circuit 14 is arranged to automatically temporarily disable (i.e. switch off) the automatic capture routine for the heart chamber in question on the basis of at least one or the following criteria:

a1) if the control circuit 14 automatically performs more than a predetermined number of threshold searches during a certain time, b1) if the evoked response signals sensed vary more than a predetermined amount over a certain number of time cycles, c1) if a certain variable time delay, such as the AV or VV delay, with which the device 10 operates is changed such that a pacing pulse may be delivered by the device 10 during the time window when an evoked response is to be sensed, in such a manner that the detection of the evoked response will be unreliable.

For example, consider the right atrium RA, which now may be called a first heart chamber. The corresponding sensing and pacing circuits 25, 27 can then be called first sensing and pacing circuits. The control circuit 14 is arranged to carry out an automatic capture routine for the right atrium RA which includes an adaptation of a pacing regime, which involves said first pacing circuit 27, in dependence on the sensing with said first sensing circuit 25 during a first ER time window. This automatic capture routine is automatically temporarily disabled (switched off):

a1) if the control circuit 14 automatically performs more than a predetermined number of threshold searches with said first pacing circuit 27 and said first sensing circuit 25 during a certain time.

b1) if the evoked response signals sensed by said first sensing circuit 25 vary more than a predetermined amount over a certain number of time cycles, c1) if a certain variable time delay with which the device 10 operates is changed such that a pacing pulse may be delivered by the device 10 during said first time window in such a manner that the detection of the evoked response with said first sensing circuit 25 during said first time window is likely to be unreliable.

Concerning a1)

The fact that many threshold searches are performed may indicate that the automatic capture routine does not work properly. Therefore, the automatic capture routine is switched off. The criteria can for example be that more that 10 threshold searches have been performed within one hour.

The control circuit 14 is also arranged to automatically end the temporary disablement of the automatic capture routine (i.e. to switch on the automatic capture routine). The control circuit 14 can for example end the disablement if a certain predetermined time has passed (for example 8 hours) or if the evoked response signals sensed by the sensing circuit 25 appears to be stable (vary less than a predetermined amount over a certain number of time cycles).

Concerning b1)

The fact that the evoked response signals vary may for example be caused by moving leads (so-called micro dislodgements). If the evoked response signals vary too much, an automatic capture routine can be unreliable. Therefore, this automatic capture routine is switched off. For example a suitable mathematical measure of variation can be used (i.e. the variation of the evoked response signal values over several time cycles is determined). If this variation exceeds a predetermined value, the automatic capture routine is switched off.

Similarly to the case a1), also concerning the case b1), the control circuit 14 can be arranged to automatically end the temporary disablement of the automatic capture routine. The control circuit 14 can for example end the disablement if a certain predetermined time has passed (for example 8 hours) or if the evoked response signals sensed by the sensing circuit 25 appears to be stable (vary less than a predetermined amount over a certain number of time cycles).

Concerning c1)

The device may for example operate with a variable AV delay. If the AV delay is changed such that a possible pacing pulse delivered with a second pacing circuit 37 and/or 47 will be delivered during the time window during which an evoked response is to be sensed with the help of the sensing circuit 25, in such a manner that the detection of the evoked response is likely to be unreliable, then said automatic capture routine, which is related to the pacing and sensing circuits 27, 25, will be temporarily disabled. The device 10 may be programmed with predefined criteria, as to whether the detection is likely to be unreliable. It is for example possible to consider the detection to be likely to be unreliable as soon as a pacing pulse may be delivered by any pacing circuit of the device during the time window for sensing an evoked response with the sensing circuit in question.

Similarly to the case a1) and b1), also concerning the case c1), the control circuit 14 can be arranged to automatically end the temporary disablement of the automatic capture routine. The control circuit 14 can end the disablement when the AV delay has changed such that it is no longer the case that a pacing pulse may be delivered during the evoked response time window.

It can be noted that the device 10 can be set to operate with some "hysteresis" in order to prevent a too frequent switching off and on of the automatic capture routine. This can for example be done by programming a minimum time that has to pass before the mode is changed a second time, i.e. before the automatic capture routine is switched from on to off and to on again, or vice versa.

As mentioned above, the control circuit 14 is arranged to be able to carry out similar capture routines concerning each channel of the device 10. The capture routine for the respective channel is temporarily disabled, and the disablement ends, in the same manner as described above for the channel related to the right atrium RA. Furthermore, the automatic capture routines related to the different channels operate independently of each other such that the automatic capture routine is automatically temporarily disabled only in that pacing/sensing channel where the criterion or criteria indicate that the automatic capture routine should be temporarily disabled. The disablement also ends in each channel independently of the other channels.

According to the above example, the right atrium RA was considered a first heart chamber. In an analogous manner, instead for example the right ventricle RV can be considered a first heart chamber. The corresponding sensing and pacing circuits 35, 37 can then be called first sensing and pacing circuits. Similarly to the above, the control circuit 14 is arranged to carry out an automatic capture routine for the right ventricle RV.

The device may operate with a variable VV delay. If the VV delay is changed such that a possible pacing pulse delivered with a second ventricular pacing circuit 47 will be delivered during the time window during which an evoked response is to be sensed with the help of the sensing circuit 35, in such a manner that the detection of the evoked response is likely to be unreliable, then said automatic capture routine which is related to the pacing and sensing circuits 37, 35 will be temporarily disabled.

Figure 3:
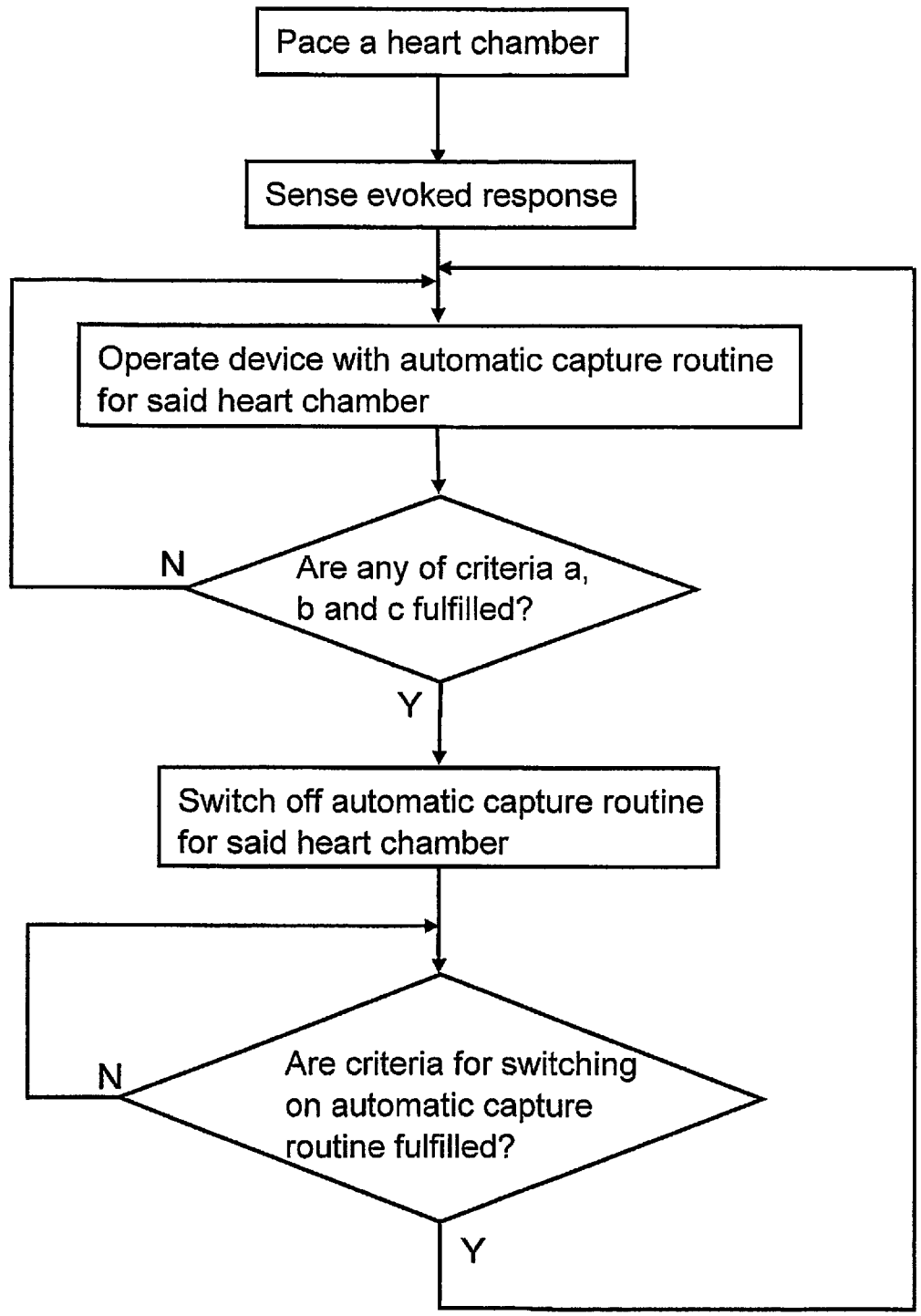
FIG. 3 illustrates schematically a method according to the invention.

An example of a method of operating an implantable heart stimulating device 10 according to the invention will now be described with reference to FIG. 3.

The devices operates with time cycles corresponding to heart cycles.

Pacing pulses are delivered to a first heart chamber (the "delivery" of pacing pulses also includes the possibility that the pacing pulses can be inhibited if intrinsic depolarizations are detected).

Evoked responses from the first heart chamber are sensed by sensing during a first time window that follows after a delivered pacing pulse.

An automatic capture routine for the heart chamber is carried out, which automatic capture routine includes an adaptation of a pacing regime regarding said first heart chamber in dependence on the sensing for evoked responses from said first heart chamber during said first time window.

A decision is made whether to disable the automatic capture routine for said first heart chamber. This decision is based on at least one of the following criteria:

a1) if more than a predetermined number of threshold searches are automatically performed for the first heart chamber during a certain time, for example more than 10 searches during one hour, b1) if the sensed evoked response signals from the first heart chamber vary more than a predetermined amount over a certain number of time cycles, c1) if a certain variable time delay, such as an AV delay or a VV delay, with which the device 10 operates is changed such that a pacing pulse may be delivered by the device 10 to some other heart chamber during said first time window, such that the detection of the evoked response from the first heart chamber during the first time window is likely to be unreliable.

If the decision is that the automatic capture routine should be disabled (i.e. not used), then later a new decision is made as to whether the automatic capture routine can start again. The decision can be based on the same kind of criteria as those described above in connection with the device according to the invention.

The above mentioned method is performed independently for each heart chamber for which pacing/sensing is carried out.

The method according to the invention need not be described in more detail, since the method to a large extent corresponds to the above described manner of how the device according to the invention operates.

Although modifications and changes may be suggested by those skilled in the art, it is the intention of the inventor to embody within the patent warranted heron all changes and modifications as reasonably and properly come within the scope of his contribution to the art.

I claim as my invention:

1. An implantable heart stimulating device comprising:
a pacing circuit configured to communicate with a pacing electrode configured for positioning in or at a heart chamber, said pacing circuit being configured to pace the heart chamber via the pacing electrode;
a sensing circuit that communicates with at least one sensing electrode or sensor configured to be positioned relative to said heart chamber;
a control circuit being configured to detect an evoked response to a pacing pulse delivered by said pacing circuit by sensing, with said sensing circuit, within a time window that follows after a pacing pulse delivered by the pacing circuit;
said control circuit being configured to operate with time cycles corresponding to cardiac cycles;
said control circuit being configured to execute an automatic capture routine, which includes adaptation of a pacing regime involving said pacing circuit, dependent on the sensing with the sensing circuit during said time window;
said automatic capture routing comprising delivering a back-up pacing pulse if no evoked response is sensed within a relevant time window; and
said control circuit being configured to automatically temporarily disable the delivery of a back-up pacing pulse involving said pacing circuit and said sensing circuit, dependent on at least one of the following criteria:
a1) if the control circuit automatically performs more than a predetermined number of threshold searches with said pacing circuit and said sensing circuit during a predetermined time, and
b1) if a variable time delay, with which said control circuit operates, is changed to cause a pacing pulse to be delivered during said time window such that detection of the evoked response with said sensing circuit during said time window is likely to be unreliable.

2. An implantable heart stimulating device as claimed in claim 1 wherein said pacing circuit is a first pacing circuit, said pacing electrode is a first pacing electrode, and said heart chamber is a first heart chamber, and comprising a second pacing circuit that communicates with a second pacing electrode configured to be positioned relative to a second heart chamber, said second pacing circuit being configured to pace said second heart chamber via said second pacing electrode.

3. An implantable heart stimulating device as claimed in claim 2 wherein said sensing circuit is a first sensing circuit and wherein said time window is a first time window, and wherein said implantable heart stimulating device comprises:
a second sensing circuit that communicates with at least one sensing electrode or sensor configured to be positioned relative to the second heart chamber; and
said control circuit is configured to detect an evoked response to a pacing pulse delivered by the second pacing circuit by sensing, with said second sensing circuit within a second time window that follows after a pacing pulse delivered by the second pacing circuit; and
said control circuit is configured to implement an automatic capture routine that includes adaptation of a pacing regime involving said second pacing circuit, dependent on said sensing with said second sensing circuit during said second time window.

4. An implantable heart stimulating device as claimed in claim 3 wherein said control circuit is configured to automatically temporarily disable the delivery of a back-up pacing pulse involving said second pacing circuit and said second sensing circuit dependent on at least one of the following criteria:
a2) if the control circuit automatically performs more than one predetermined number of threshold searches with said second pacing circuit and said second sensing circuit during a predetermined time,
b2) if the evoked response signal sensed by the second sensing circuit varies more than a predetermined amount over a predetermined number of time cycles, and
c2) if a variable time delay within which said control circuit operates is changed such that a pacing pulse may be delivered during said second time window such detection of the evoked response with the second sensing circuit during the second time window is likely to be unreliable.

5. An implantable heart stimulating device as claimed in claim 4 wherein said control circuit is configured to execute said automatic capture routine involving said first pacing circuit and said first sensing circuit and said automatic capture routine involving said second pacing circuit and said second sensing circuit independently of each other.

6. An implantable heart stimulating device as claimed in claim 3 wherein said control circuit is configured to temporarily disable the delivery of a back-up pacing pulse at least on the basis of (b1), and wherein said variable time delay is an AV delay between an atrial event and delivery of a ventricular pacing pulse, wherein said first heart chamber is an atrium, said first pacing circuit and said first sensing circuit comprise an atrial channel, and said second heart chamber is a ventricle, and said second pacing circuit and said second sensing circuit comprise a ventricular channel, said control circuit being configured, if said AV delay is changed so that a pacing pulse delivered with said second pacing circuit will be delivered during said first time window so that detection of the evoked response by the first sensing circuit during the first time window is likely to be unreliable, to temporarily disable the delivery of a back-up pacing pulse involving said first pacing circuit and said first sensing circuit.

7. An implantable heart stimulating device as claimed in claim 3 wherein said control circuit is configured to temporarily disable the delivery of a back-up pacing pulse at least on the basis of (b1), wherein said variable time delay is a VV delay between a ventricular event related to one of two ventricular channels and delivery of a ventricular pacing pulse in another of said two ventricular channels, wherein said first heart chamber is one ventricle and said first pacing circuit and said first sensing circuit comprise one of said ventricular channels, and said second heart chamber is another ventricle and said second pacing circuit and said second sensing circuit comprise another of said ventricular channels, and wherein said control circuit is configured, if said VV delay changes so that a pacing pulse delivered by said second pacing circuit is delivered during said first time window such that detection of an evoked response with said first sensing circuit during said first time window is likely to be unreliable, to temporarily disable the delivery of a back-up pacing pulse.

8. An implantable heart stimulating device as claimed in claim 4 wherein said control circuit is configured to temporarily disable the delivery of a back-up pacing pulse at least on the basis of (a1) and/or (a2) and wherein said control circuit is configured to automatically end the temporary disablement based on a further criteria selected from the group consisting of if a predetermined time period has elapsed, and if evoked response signals sensed by either the first or second sensing circuit vary by less than a predetermined amount over a predetermined number of time cycles.

9. An implantable heart stimulating device as claimed in claim 4 wherein said control circuit is configured to temporarily disable the delivery of a back-up pacing pulse at least on the basis of (b2) and wherein said control circuit is configured to automatically end the temporary disablement based on a further criteria selected from the group consisting of if a predetermined time period has elapsed, and if evoked response signals sensed by either the first or second sensing circuit vary by less than a predetermined amount over a predetermined number of time cycles.

10. An implantable heart stimulating device as claimed in claim 4 wherein said control circuit is configured to temporarily disable at least one of the respective delivery of a back-up pacing pulse dependent on at least (b1) and/or (c2), and wherein said control circuit is configured to automatically end the temporary disablement when said time delay changes so that a pacing pulse may no longer be delivered during said first time window or during said time window that would make detection of an evoked response by said first sensing circuit or said second sensing circuit, respectively, likely to be unreliable.

11. A method for operating an implantable heart stimulating device comprising:
   implanting a heart stimulating device in a subject;
   implanting a pacing electrode in or at a heart chamber, and pacing the heart chamber via the pacing electrode with a pacing circuit in the heart stimulating device;
   positioning at least one sensing electrode or sensor relative to said heart chamber;
   detecting an evoked response to a pacing pulse delivered by said pacing circuit by sensing, with a sensing circuit in the heart stimulating device, within a time window that follows after a pacing pulse delivered by the pacing circuit;
   operating a control unit in said heart stimulating device with time cycles corresponding to cardiac cycles and, with said control circuit, executing an automatic capture routine, which includes adaptation of a pacing regime involving said pacing circuit, dependent on the sensing with the sensing circuit during the first time window;
   said automatic capture routing comprising delivering a back-up pacing pulse if no evoked response is sensed within a relevant time window; and
   from said control circuit, automatically temporarily disabling the delivery of a back-up pacing pulse involving said pacing circuit and said sensing circuit, dependent on at least one of the following criteria:
   a1) if the control circuit automatically performs more than a predetermined number of threshold searches with said pacing circuit and said sensing circuit during a predetermined time, and
   b1) if a variable time delay, with which said control circuit operates, is changed to cause a pacing pulse to be delivered during said time window such that detection of the evoked response with said sensing circuit during said time window is likely to be unreliable.

12. A method for operating an implantable heart stimulating device as claimed in claim 11 wherein said pacing circuit is a first pacing circuit, said pacing electrode is a first pacing electrode, and said heart chamber is a first heart chamber, and comprising placing a second pacing electrode relative to a second heart chamber, and pacing said second heart chamber via said second pacing electrode with a second pacing circuit in the heart stimulating device.

13. A method for operating an implantable heart stimulating device as claimed in claim 12 wherein said sensing circuit is a first sensing circuit and wherein said time window is a first time window, and comprising:
   positioning at least one further sensing electrode or sensor configured relative to the second heart chamber; and
   detecting an evoked response to a pacing pulse delivered by the second pacing circuit by sensing, with a second sensing circuit in the heart stimulating device within a second time window that follows after a pacing pulse delivered by the second pacing circuit; and
   with said control circuit, executing an automatic capture routine that includes adaptation of a pacing regime involving said second pacing circuit, dependent on said sensing with said second sensing circuit during said second time window.

14. A method for operating an implantable heart stimulating device as claimed in claim 13 wherein, from said control circuit, automatically temporarily disabling the delivery of a back-up pacing pulse involving said second pacing circuit and said second sensing circuit dependent on at least one of the following criteria:
   a2) if the control circuit automatically performs more than one predetermined number of threshold searches with said second pacing circuit and said second sensing circuit during a predetermined time,
   b2) if the evoked response signal sensed by the second sensing circuit varies more than a predetermined amount over a predetermined number of time cycles, and
   c2) if a variable time delay within which said control circuit operates is changed such that a pacing pulse may be delivered during said second time window such detection of the evoked response with the second sensing circuit during the second time window is likely to be unreliable.

15. A method for operating an implantable heart stimulating device as claimed in claim 14 comprising, from said control circuit, executing said automatic capture routine involving said first pacing circuit and said first sensing circuit and said automatic capture routine involving said second pacing circuit and said second sensing circuit independently of each other.

16. A method for operating an implantable heart stimulating device as claimed in claim 13 comprising, from said control circuit, temporarily disabling the delivery of a back-up pacing pulse at least on the basis of (b1), and wherein said variable time delay is an AV delay between an atrial event and delivery of a ventricular pacing pulse, wherein said first heart chamber is an atrium, said first pacing circuit and said first sensing circuit comprise an atrial channel, and said second heart chamber is a ventricle, and said second pacing circuit and said second sensing circuit comprise a ventricular channel, and from said control circuit, if said AV delay is changed so that a pacing pulse delivered with said second pacing circuit will be delivered during said first time window so that detection of the evoked response by the first sensing circuit during the first time window is likely to be unreliable, temporarily disabling the delivery of a back-up pacing pulse involving said first pacing circuit and said first sensing circuit.

17. A method for operating an implantable heart stimulating device as claimed in claim 13 comprising, from said control circuit, temporarily disabling the delivery of a back-up pacing pulse at least on the basis of (b1), wherein said variable time delay is a VV delay between a ventricular event related to one of two ventricular channels and delivery of a ventricular pacing pulse in another of said two ventricular channels, wherein said first heart chamber is one ventricle and said first pacing circuit and said first sensing circuit comprise one of said ventricular channels, and said second heart chamber is another ventricle and said second pacing circuit and said second sensing circuit comprise another of said ventricular channels, and from said control circuit, if said VV delay changes so that a pacing pulse delivered by said second pacing circuit is delivered during said first time window such that detection of an evoked response with said first sensing circuit during said first time window is likely to be unreliable, temporarily disabling the delivery of a back-up pacing pulse.

18. A method for operating an implantable heart stimulating device as claimed in claim 14 comprising, from said control circuit, temporarily disabling the respective delivery of a back-up pacing pulses at least on the basis of (a1) and/or (a2) and automatically ending the temporary disablement based on a further criteria selected from the group consisting of if a predetermined time period has elapsed, and if evoked response signals sensed by either the first or second sensing circuit vary by less than a predetermined amount over a predetermined number of time cycles.

19. A method for operating an implantable heart stimulating device as claimed in claim 14 comprising, from said control circuit, temporarily disabling the respective delivery of a back-up pacing pulses on the basis of (b2) and automatically ending the temporary disablement based on a further criteria selected from the group consisting of if a predetermined time period has elapsed, and if evoked response signals sensed by either the first or second sensing circuit vary by less than a predetermined amount over a predetermined number of time cycles.

20. A method for operating an implantable heart stimulating device as claimed in claim 14 comprising, from said control circuit temporarily disabling at least one of the respective delivery of a back-up pacing pulses dependent on at least (b1) and/or (c2), and automatically ending the temporary disablement when said time delay changes so that a pacing pulse may no longer be delivered during said first time window or during said time window that would make detection of an evoked response by said first sensing circuit or said second sensing circuit, respectively, likely to be unreliable.

21. An implantable heart stimulating device comprising:
a pacing circuit configured to communicate with a pacing electrode configured for positioning in or at a heart chamber, said pacing circuit being configured to pace the heart chamber via the pacing electrode;
a sensing circuit that communicates with at least one sensing electrode or sensor configured to be positioned relative to said heart chamber;
a control circuit being configured to detect an evoked response to a pacing pulse delivered by said pacing circuit by sensing, with said sensing circuit, within a time window that follows after a pacing pulse delivered by the pacing circuit;
said control circuit being configured to operate with time cycles corresponding to cardiac cycles;
said control circuit being configured to execute an automatic capture routine, which includes adaptation of a pacing regime involving said pacing circuit, dependent on the sensing with the sensing circuit during said time window;
said automatic capture routing comprising delivering a back-up pacing pulse if no evoked response is sensed within a relevant time window; and
said control circuit being configured to automatically temporarily disable the delivery of a back-up pacing pulse involving said pacing circuit and said sensing circuit, if a variable time delay, with which said control circuit operates, is changed to cause a pacing pulse to be delivered during said time window such that detection of the evoked response with said sensing circuit during said time window is likely to be unreliable.

22. A method for operating an implantable heart stimulating device comprising:
implanting a heart stimulating device in a subject;
implanting a pacing electrode in or at a heart chamber, and pacing the heart chamber via the pacing electrode with a pacing circuit in the heart stimulating device;
positioning at least one sensing electrode or sensor relative to said heart chamber;
detecting an evoked response to a pacing pulse delivered by said pacing circuit by sensing, with a sensing circuit in the heart stimulating device, within a time window that follows after a pacing pulse delivered by the pacing circuit;
operating a control unit in said heart stimulating device with time cycles corresponding to cardiac cycles and, with said control circuit, executing an automatic capture routine, which includes adaptation of a pacing regime involving said pacing circuit, dependent on the sensing with the sensing circuit during the first time window;
said automatic capture routing comprising delivering a back-up pacing pulse if no evoked response is sensed within a relevant time window; and
from said control circuit, automatically temporarily disabling the delivery of a back-up pacing pulse involving said pacing circuit and said sensing circuit, if a variable time delay, with which said control circuit operates, is changed to cause a pacing pulse to be delivered during said time window such that detection of the evoked response with said sensing circuit during said time window is likely to be unreliable.

* * * * *